US012642801B2

(12) United States Patent
Kim et al.

(10) Patent No.: US 12,642,801 B2
(45) Date of Patent: Jun. 2, 2026

(54) PHARMACEUTICAL COMPOSITION FOR PREVENTING OR TREATING RHEUMATOID ARTHRITIS AND HEALTH FUNCTIONAL FOOD

(71) Applicant: SEOUL NATIONAL UNIVERSITY R&DB FOUNDATION, Seoul (KR)

(72) Inventors: Hong Hee Kim, Gyeonggi-do (KR); Min Kyung Kim, Gyeonggi-do (KR); Su Han Jung, Seoul (KR); Seo Jin Hong, Gyeonggi-do (KR); Ji Sun Jang, Seoul (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 853 days.

(21) Appl. No.: 17/941,156

(22) Filed: Sep. 9, 2022

(65) Prior Publication Data

US 2023/0111232 A1 Apr. 13, 2023

Related U.S. Application Data

(63) Continuation of application No. PCT/KR2022/008269, filed on Jun. 13, 2022.

(30) Foreign Application Priority Data

Oct. 13, 2021 (KR) ........................ 10-2021-0135956

(51) Int. Cl.

*A61K 31/519* (2006.01)
*A23L 33/00* (2016.01)
*A23L 33/10* (2016.01)
*A61P 19/02* (2006.01)
*A61P 37/06* (2006.01)

(52) U.S. Cl.

CPC ............ *A61K 31/519* (2013.01); *A23L 33/10* (2016.08); *A23L 33/40* (2016.08); *A61P 19/02* (2018.01); *A61P 37/06* (2018.01); *A23V 2002/00* (2013.01)

(58) Field of Classification Search

CPC ........ A61K 31/519; A61P 19/02; A61P 37/06; A23V 2002/00; A23L 33/10; A23L 33/40

See application file for complete search history.

(56) References Cited

U.S. PATENT DOCUMENTS

| | | | |
|---|---|---|---|
| 2015/0045370 A1 | 2/2015 | Cohen et al. | |
| 2024/0239828 A1* | 7/2024 | Wiles | C07H 13/04 |

FOREIGN PATENT DOCUMENTS

| | | |
|---|---|---|
| KR | 10-2019-0087808 A | 7/2019 |
| WO | WO 2018/009544 A1 | 1/2018 |
| WO | WO 2019/105886 A1 | 6/2019 |

OTHER PUBLICATIONS

Office action issued on Mar. 27, 2025 from Korean Patent Office in a counterpart Korean Patent Application No. 10-2021-0135956 (all the cited references are listed in this IDS.) (English translation is also submitted herewith.).

Thomas B. Sundberg et al., "Development of Chemical Probes for Investigation of Salt-Inducible kinase Function in Vivo", ACS Chemical Biology, vol. 11, pp. 2105-2111, 2016.

Darling, N. et al., "Nuts and bolts of the salt-inducible kinases (SIKs)", The Biochemical journal, 2021, 487(7), pp. 1377-1397, DOI:10.1042/BCJ20200502.

Lombardi, M. S. et al., "Salt-inducible kinases (SIK) inhibition reduces RANKL-induced osteoclastogenesis", PLOS one, 2017, 12(10): e0185426, pp. 1-18, https://doi.org/10.1371/journal.pone.0185426.

* cited by examiner

*Primary Examiner* — Erich A Leeser

(74) *Attorney, Agent, or Firm* — The PL Law Group, PLLC

(57) ABSTRACT

A pharmaceutical composition for preventing or treating rheumatoid arthritis and a health functional food for preventing or improving rheumatoid arthritis, specifically, proposes specific administration methods and administration dosages of the above composition, and demonstrates immune reaction regulatory functions of the composition according to the present invention and inflammation inhibitory effects by the same through rheumatoid arthritis animal models.

2 Claims, 11 Drawing Sheets

PHARMACEUTICAL COMPOSITION FOR PREVENTING OR TREATING RHEUMATOID ARTHRITIS AND HEALTH FUNCTIONAL FOOD

PRIORITY

The present application is a continuation of application to International Application No. PCT/KR2022/008269 with an International Filing Date of Jun. 13, 2022, which claims the benefit of Korean Patent Application No. 10-2021-0135956 filed on Oct. 13, 2021 at the Korean Intellectual Property Office, the disclosures of which are incorporated by reference herein in their entirety.

BACKGROUND

1. Technical Field

The present invention relates to a pharmaceutical composition for prevention or treatment of rheumatoid arthritis.

Further, the present invention relates to a health functional food for prevention or improvement of rheumatoid arthritis.

2. Background Art

Rheumatoid arthritis (RA) is a disease in relation to loss of systemic immunological self-tolerance, and causes symptoms characterized by activation of auto-reactive immune cells on joint sites rich in collagen, as well as chronic and destructive inflammation on the joint. Rheumatoid arthritis causes cartilage injury of the joint and bone erosion due to continued chronic inflammation response in a synovial membrane, eventually, entails major clinical characteristics such as joint injury, that is, rheumatoid diseases, resulting in functional disorder.

Recently, therapeutic methods of rheumatoid arthritis are divided into general conservative therapy, drug therapy, and surgical therapy. In general, the treatment of rheumatoid arthritis is conducted for the purpose of minimizing joint pain and deformation, functional loss, etc. and restoring patients to normal life.

In this regard, current RA drug therapy uses anti-TNF-α drug and methotrexate, etc. as representative medicament. However, if patient compliance is deteriorated or does not reach clinical remission, it does not attain analgesic effects, entails a disadvantage in that symptoms such as fever or edema cannot be early inhibited, and is known to cause side effects, that is, abnormal reactions in a digestive system, musculoskeletal system, renal and endocrine system.

In other words, in spite of extensive and active researches, any obvious pathological mechanism as causes of disease in regard to the rheumatoid arthritis has yet to be discovered, therefore, it is now a state of absence for ultimate therapeutics, and a development region of therapeutics to replace the existing treatment agents is of very wide.

Thereby, in the studies to develop novel therapeutics for rheumatoid arthritis through control of inflammatory immune cells, the present inventors have confirmed rheumatoid arthritis treatment effects of a compound YKL-05-099, which is an inhibitory agent of salt-inducible kinase (SIK) as one type of protein kinases, and therefore, the present invention has been completed on the basis of the confirmation. The above protein kinase is an enzyme to catalyze phosphorylation of hydroxyl groups positioned at tyrosine, serine and threonin residues. Further, it is known that mutation or overexpression of specific protein kinase collapses a signal transmission system in normal cells (mostly a state in which in vivo signaling is continued), hence causing different diseases such as cancer, inflammation, metabolic diseases, cerebropathia or the like.

SUMMARY

An object of the present invention is to provide a novel and effective pharmaceutical composition for prevention or treatment of rheumatoid arthritis.

Another object of the present invention is to provide a novel and effective health functional food for prevention or improvement of rheumatoid arthritis.

1. A pharmaceutical composition for prevention or treatment of rheumatoid arthritis, including: a compound represented by Formula 1 below or a pharmaceutically acceptable salt thereof;

[Formula 1]

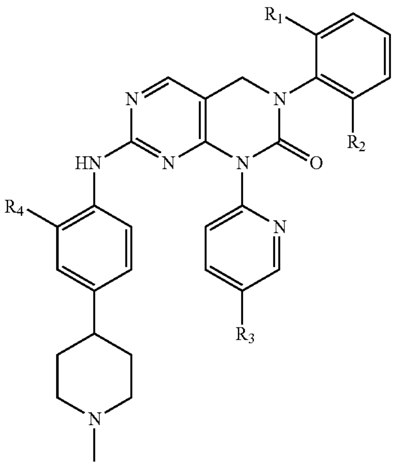

(wherein $R_1$ and $R_2$ are each independently halogen element or alkyl group having 1 to 6 carbons, and $R_3$ and $R_4$ are each independently alkoxy group having 1 to 6 carbons).

2. The composition according to the above 1, wherein the halogen element is chlorine.

3. The composition according to the above 1, wherein the compound in the composition is administered in an amount of 0.8 to 1.6 mg per 1 kg by weight of a subject in need of administration once each day.

4. A health functional food for prevention or improvement of rheumatoid arthritis, including: a compound represented by Formula 1 below or a sitologically acceptable salt thereof;

[Formula 1]

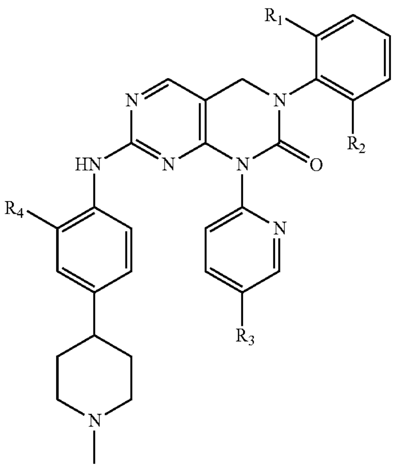

(wherein $R_1$ and $R_2$ are each independently halogen element or alkyl group having 1 to 6 carbons, and $R_3$ and $R_4$ are each independently alkoxy group having 1 to 6 carbons).

The composition according to embodiments of the present invention can be used for medicine to prevent or treat rheumatoid arthritis.

The composition according to embodiments of the present invention can be used for the health functional food to prevent or improve rheumatoid arthritis.

DETAILED DESCRIPTION

Figure 1:
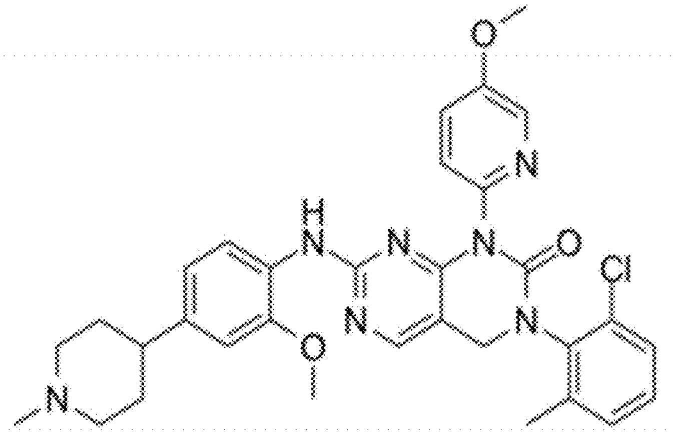
FIG. 1 illustrates a structure of compound YKL-05-099.

Hereinafter, the present invention will be described in detail.

The present invention relates to a pharmaceutical composition for prevention or treatment of rheumatoid arthritis, which includes a compound represented by Formula 1 below or a pharmaceutically acceptable salt thereof:

[Formula 1]

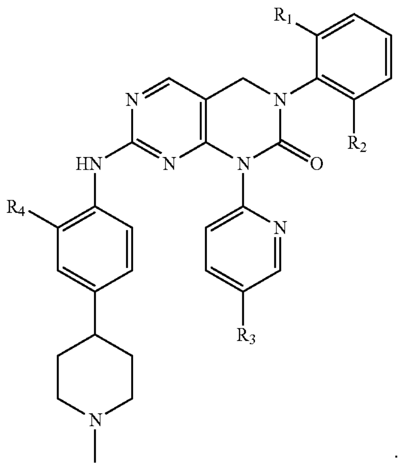

(wherein $R_1$ and $R_2$ are each independently halogen element or alkyl group having 1 to 6 carbons, and $R_3$ and $R_4$ are each independently alkoxy group having 1 to 6 carbons).

The "each independently" means that individual substituents may be optionally selected from the above substituents without influence on one another.

The "halogen element" means fluorine, chlorine, bromine or iodine, and preferably, chlorine.

The "alkyl group" means any linear or branched alkyl group containing 1 to 6 carbon atoms, preferably 1 to 4 carbon atoms, for example, may be methyl, ethyl, n-propyl, isopropyl, n-butyl, tert-butyl, n-pentyl, n-hexyl or isomers thereof, and more preferably, methyl.

The "alkoxy group" means that an oxygen atom is bound to the "alkyl group" to be connected to another group, for example, may be methoxy, ethoxy, propyloxy, i-propyloxy, n-butyloxy, tert-butyloxy, n-pentyloxy, n-hexyloxy or isomers thereof, and preferably, methoxy.

The "rheumatoid arthritis" means a chronic inflammatory systemic disease characterized by continued inflammatory response of a synovial membrane in the joint ("synovium"), and may generally be autoimmune chronic, inflammatory or systemic disease, which invades other connective tissues as well as the synovial membrane. In the early stage of rheumatoid arthritis, inflammation may occur in the synovium surrounding the joint or may be gradually propagated to nearby cartilages and bones, which may in turn cause destruction and deformation of the joint. The inflammation may occur in the joint synovium or other tissues included in the joint, but it is not limited thereto.

The "joint" refers to a site through which bones are connected, and may consist of a cartilage, a joint capsule, a synovium, a ligament, a tendon, a muscle, etc.

The "joint fluid or synovial fluid" refers to a liquid including a viscous liquid and cell ingredients generated from the joint synovium.

The subject to whom the inventive composition is used may include all animals such as rats, mice, domestic animals, etc. including human, in that the rheumatoid arthritis has already occurred or may possibly occur. For example, the subject may include mammals including human, but it is not limited thereto.

In the present invention, the "prevention" refers to all behavior to inhibit or delay rheumatoid arthritis.

In the present invention, the "treatment" refers to all behavior to improve or advantageously change symptoms of the subject having the onset of rheumatoid arthritis as well as being doubtful with rheumatoid arthritis.

In the embodiments of the present invention, clinical indexes or disease-related phenotypes appearing in the onset of rheumatoid arthritis may include: 1) increase in levels of inflammatory cytokines in the blood; 2) edema of soles of paws as well as the joint; 3) expansion of spleen and lymph tissues; 4) decrease of regulatory T cells (Treg) among immune cells; 5) increase of macrophage cells among immune cells; and 6) increase in bone loss around the joint.

The cytokine described above may include: essential inflammatory cytokines to induce rheumatoid arthritis such as TNF-α and IL-6; representative immunoreactive cytokines of Th1 such as IFN-γ; or representative immunoreactive cytokines of Th17 such as IL-17a.

T-helper (Th) lymphocytes may be divided into Th1 and Th2 based on conditions of cytokine secretion, wherein Th1 cells typically secrete IFN-γ to activate macrophages or the like, which in turn induces cellular immune response, and lead differentiation of B lymphocytes thus to reinforce cellular immune response. Meanwhile, Th2 cells secrete some cytokines such as IL-4, IL-5, etc., which induce eosinophils and serve to protect against parasites, and may induce B lymphocytes to produce IgE, so as to perform parasite protection while causing allergic reaction. Production of Th17 cells is inhibited by IFN-γ and IL-4, and depends on CD28 and ICOS as cofactors for stimulation. Th17 cells secrete TNF-α along with IL-17, wherein TNF-α is an inflammatory cytokine to deteriorate different autoimmune diseases. It is known that IL-17 induces production of various inflammatory cytokines such as IL-6, IL-8, IL-15, TNF-α, VEGF, CSF, MMP, etc., which in turn results in pathogenic conditions of tissue environments, while IL-17a is a member of IL-17 family.

It is known that the regulatory T cell (Treg) may block activation of immune cells through, for example, apoptosis of active T cells, induction of metabolic disorder, suppression of dendritic cells, or the like, thereby participating in inhibition of immune response. Specifically, it may inhibit autoimmune reaction while maintaining immune-tolerance to self-antigen.

The macrophage cell is a major cell having a role in congenital immune, which has ability for intake of antigen at invasion of the antigen or for secretion of toxin to destruct the same. Further, the macrophage cell delivers the antigen to lymphocytes so as to induce immune reaction. Dysregulation of the macrophage cell may cause chronic diseases such as an autoimmune disease.

Therefore, according to the embodiments of the present invention, it could be confirmed that the inventive compound may regulate immune reaction at the onset of rheumatoid arthritis to suppress inflammation and may be effective in inhibiting damage to other tissues around the inflammation.

In the present invention, "CIA" is used for an animal model suffering from rheumatoid arthritis and means "collagen-induced arthritis."

In the present invention, "SIA" is used for an animal model suffering from rheumatoid arthritis and means "serum transfer arthritis."

The pharmaceutical composition of the present invention may include an active ingredient alone, or further include one or more pharmaceutically acceptable carriers, excipients or diluents, so as to be provided in the form of pharmaceutical composition.

The expression "pharmaceutically acceptable" means that characteristics of not impairing physical properties as well as biological activity of a compound are exhibited without arousing significant stimulation in a subject, cell, tissue, etc. to which the compound or a composition including the compound is administered.

The expression "pharmaceutically acceptable salt" refers to a salt which is prepared using any acid or base relatively non-toxic to a specific compound according to the preset invention. The pharmaceutically acceptable salt may include, for example, acid-addition salts or metal salts.

The acid-addition salts may be formed from inorganic acids such as hydrochloric acid, nitric acid, phosphoric acid, sulfuric acid, hydroacid bromide, hydroacid iodide, nitrous acid or phosphorous acid, along with non-toxic organic acids such as aliphatic mono- and di-carboxylate, phenyl-substituted alkanoate, hydroxyl alkanoate, alkanedioate, aromatic acids, aliphatic and aromatic sulfonic acids, etc. These pharmaceutically non-toxic salts may include sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maliate, butyne-1,4-dioate, hexane-1,6-dioate, benzoate, chlorobenzoate, methyl benzoate, dinitro-benzoate, hydroxy benzoate, methoxy benzoate, phthalate, terephthalate, benzene sulfonate, toluene sulfonate, chlorobenzene sulfonate, xylene sulfonate, phenyl acetate, phenyl propionate, phenyl butyrate, citrate, lactate, β_hydroxy butyrate, glycolate, malate, tartrate, methane sulfonate, propane sulfonate, naphthalene-1-sulfonate, naphthalene-2-sulfonate or mandelate. For example, an acid-addition salt of the compound represented by Formula 1 may be obtained by dissolving the compound in an excess amount of acid solution and then precipitating a salt using a hydrated organic solvent, for example, methanol, ethanol, acetone or acetonitrile.

The metal salt may be sodium, potassium or calcium salts. The metal salt may be prepared using a base, for example, an alkali-metal or alkali-earth metal salt may be obtained by dissolving the compound in an excess amount of alkali-metal hydroxide or alkali-earth metal hydroxide solution, filtering out non-soluble compound salts, evaporating and/or drying the filtrate. The pharmaceutical composition of the present invention may also be provided in combination with any therapeutic substance for rheumatoid arthritis known in the art. That is, the pharmaceutical composition of the present invention may be administered along with any known material having effects of preventing or treating rheumatoid arthritis.

A preferred administration amount (i.e., dosage) of the inventive composition may vary depending on conditions and body weight of individual having occurrence of disease, extent of the disease, form of drugs, administration route and period, etc., however, can be appropriately selected by those skilled in the art. The administration may be done once per day or divided into several times.

For example, the present invention may include a composition containing a specific compound, wherein the compound is administered in an amount of 10 to 20 mg per 1 kg of body weight of a subject in need of administration once a day with reference to mice according to the embodiments. In the case of human, since about 0.08 times of the dosage to a mouse is administered, the present invention may include the composition containing the above compound, which is administered in an amount of 0.8 to 1.6 mg per 1 kg of body weight of the subject once a day, as converted into a dosage to human.

In the present invention, the term "administration" means introducing a desired substance into an individual by any suitable method.

In the present invention, the term "subject in need of administration" means a subject to whom the inventive composition is administered for the purpose of treating or preventing rheumatoid arthritis, specifically may refer to all animals including rats, mice, livestock, etc. including human, in that the rheumatoid arthritis has already occurred or may possibly occur.

The composition of the present invention may be administered in an oral or parenteral route. For the parenteral administration, skin external application or intraperitoneal, intrarectal, subcutaneous, intravenous, intramuscular or intrathoractic injection type introduction manner is preferably adopted, but it is not limited thereto.

When formulating the composition of the present invention, the formulation may be prepared using diluents such as fillers, bulking agents, binders, wetting agents, disintegrating agents, surfactants, etc., or excipients. Solid formulations for oral administration may include tablets, pills, powder, granulates, capsules, etc., and such solid formulations may be prepared by adding at least one excipient, for example, starch, calcium carbonate, sucrose or lactose, gelatin, etc. to the extract. Further, in addition to simple excipients, lubricants such as magnesium stearate, talc, etc. may also be used. Liquid formulations for oral administration may include suspension, oral liquids, emulsifiers, syrup, etc. Other than simple diluents commonly used in the art such as water, liquid paraffin, etc., various excipients, for example, wetting agents, sweeteners, aromatic agents, preservatives, etc. may be further included. Formulations for parenteral administration may include sterile solution, non-aqueous solvents, suspension, emulsifiers, lyophilized formulation, suppositories, etc. The non-aqueous solvent used herein may include propyleneglycol, polyethyleneglycol, vegetable oil such as olive oil, injectable ester such as ethyl oleate, etc. Substrates for suppositories used herein may include witepsol, macrogol, tween 61, cacao fat, laurin fat, glycero-gelatin, etc.

Further, the preset invention relates to a health functional food for prevention or improvement of rheumatoid arthritis, which includes a compound represented by Formula 1 above or a sitologically acceptable salt thereof.

The "compound represented by Formula 1" is the same as stated above, and therefore will not be described to avoid duplication.

The expression "sitologically acceptable" means that characteristics of not impairing physical properties as well as biological activity of a compound are exhibited without arousing significant stimulation in a subject, cell, tissue, etc. to which the compound or a composition including the compound is administered.

The "sitologically acceptable salt" refers to a salt prepared using a specific compound of the present invention along with relatively non-toxic acid or base, and may be within the range of the "salts" as described above.

The health functional food may be manufactured and processed in the form of tablets, capsules, powder, granulates, liquid, pills, etc., for the purpose of preventing or improving rheumatoid arthritis.

The "health functional food" refers to foods produced and processed using raw materials or ingredients having functionality useful for human body, and means the food to be taken for the purpose of acquiring useful effects in terms of health application such as regulation of nutrients or physiological activity with respect to the structure and functions of a human body.

The health functional food of the present invention may contain conventional food additives.

The food additives may include, for example: chemical compounds such as ketones, glycine, calcium citrate, nicotic acid, cinnamic acid, etc.; natural additives such as persimmon color, licorice extract, crystalline cellulose, Kaoliang color, guar gum, etc.; composite formulations such as sodium L-glutamate preparations, alkaline preparations added to noodles, preservative preparations, tar color preparations, etc., but they are not limited thereto. For example, the health functional food in a tablet form may be manufactured by mixing the composition with excipients, binders, disintegrating agents or other additives to prepare a mixture and granulating the mixture by any conventional process, followed by compression-molding with addition of glydents or the like, otherwise, directly compressing and molding the mixture. Further, the health functional food in the tablet form may additionally contain a flavoring agent if needed.

Alternatively, among the health functional foods in capsule forms, a hard capsule formulation may be manufactured by mixing the composition with additives such as excipients or the like to prepare a mixture, and then filling a typical hard capsule with the mixture. Meanwhile, a soft capsule formulation may be manufactured by mixing the composition with additives such as excipients or the like to prepare a mixture, and then filling a capsule substrate such as gelatin with the mixture. The soft capsule formulation may additionally contain a plasticizer such as glycerin or sorbitol, a coloring agent, a preservative, etc. if needed.

Further, the health functional food in a pill form may be manufactured by mixing the composition with excipients, binders, disintegrating agents, etc. to prepare a mixture, and then molding the mixture by any conventional process. Further, if necessary, the surface of the pill may be peeled off using white sugar or other peeling agents. Otherwise, the surface of the pill may be coated with starch, talc, etc.

Further, the health functional food in a granule form may be manufactured by mixing the composition with excipients, binders, disintegrating agents, etc. to prepare a mixture, and then forming the mixture into granulates by the existing process, and may additionally contain fragrant ingredients, a flavoring agent, etc. if needed.

Examples of the health functional food may include beverages, meats, chocolates, foods, confectionaries, pizza, instant noodles, other noodles, gums, candies, ice creams, alcoholic drink, vitamin complex and health supplement foods.

Hereinafter, the present invention will be described in detail by way of the following examples.

EXAMPLES

In the examples of the present invention, efficacies of the composition of the present invention were investigated by establishing animal models CIA or SIA with animal diseases similar to rheumatoid arthritis of the human body. Specifically, 100 μl of 250 μg or 500 μg of the compound YKL-05-099 (CAS No.: 1936529-65-5) shown in FIG. 1 was intraperitoneally (i.p.) administered to a mouse weighed 25 g (that is, 10 mg or 20 mg per 1 kg) once a day.

1. Mitigation Effects of Edema of Soles and Joint

Figure 2:
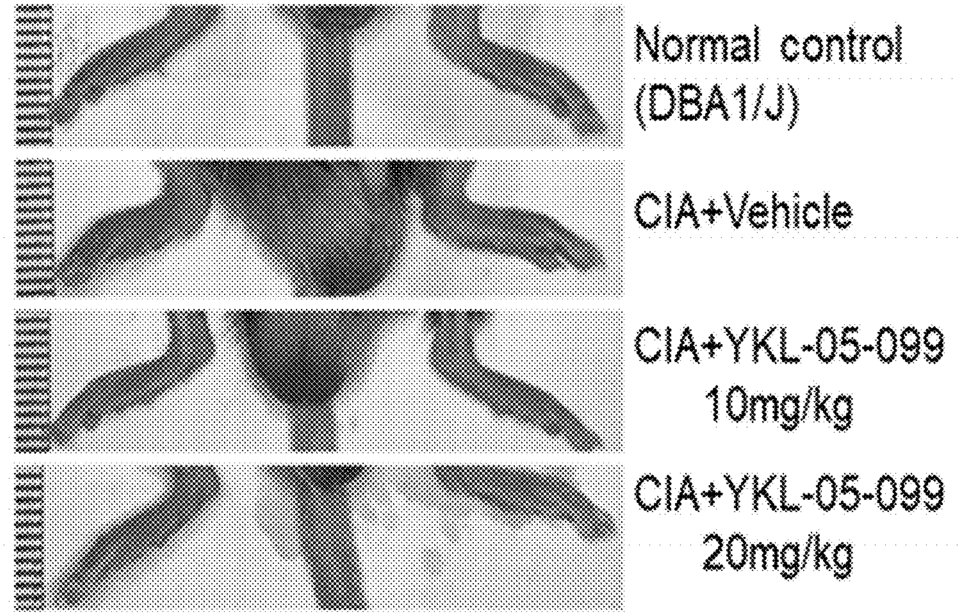
FIG. 2 is photographs showing effects of improving edema around paws and joints of CIA mice in the embodiments of the present invention.
Figure 3:
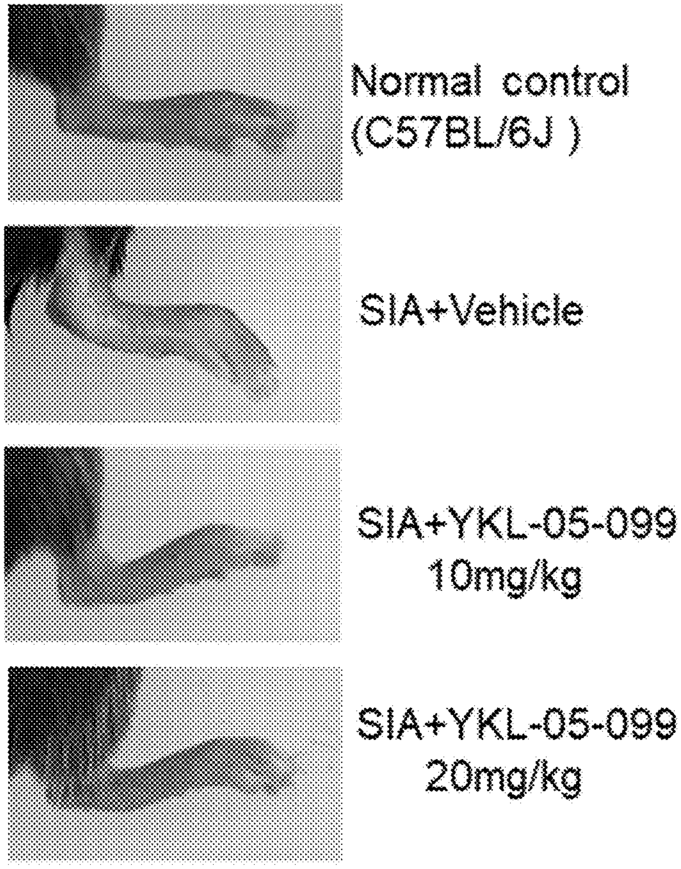
FIG. 3 is photographs showing effects of improving edema around paws and joints of SA mice in the embodiments of the present invention.

After i.p. administration of YKL-05-099 in an amount of 10 mg/kg or 20 mg/kg to mice having rheumatoid arthritis once a day, improvement of edema in the paws was investigated. For definite measurement and comparison, the most swollen portion of the paw was measured in multiple times, and collected numerical values of paw thickness were recorded and compared. Disease-free mice without administration of antigens were used as a negative control. From FIGS. 2 and 3, it could be visually observed that the edema of the paws and around the joints in CIA mice and SIA mice, respectively, was remarkably improved as compared to the control.

Figure 4:
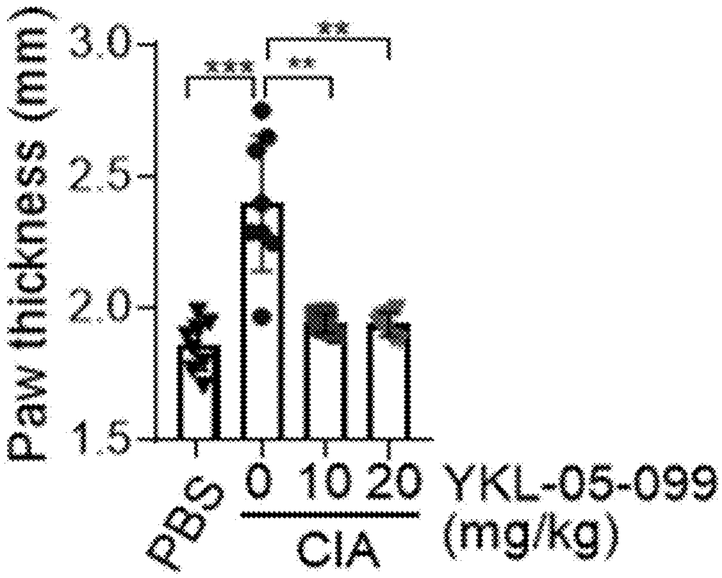
FIG. 4 illustrates measured results of paw thickness of CIA mice in the embodiments of the present invent ion.
Figure 5:
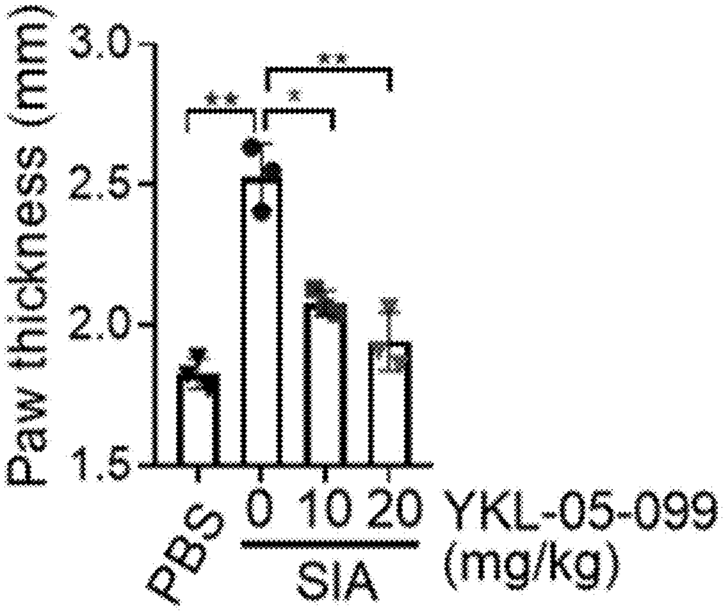
FIG. 5 illustrates measured results of paw thickness of SIA mice in the embodiments of the present invention.

FIG. 4 illustrates measured results of the paw thickness of CIA mice while FIG. 5 illustrates measured results of the paw thickness of SIA mice, respectively. It could be confirmed that the YKL-05-099 administered group has remarkably thinner paw thickness than the vehicle administered group, thus to exhibit edema inhibition effects.

2. Observation of Rheumatoid Arthritis Clinical Scores

Figure 6:
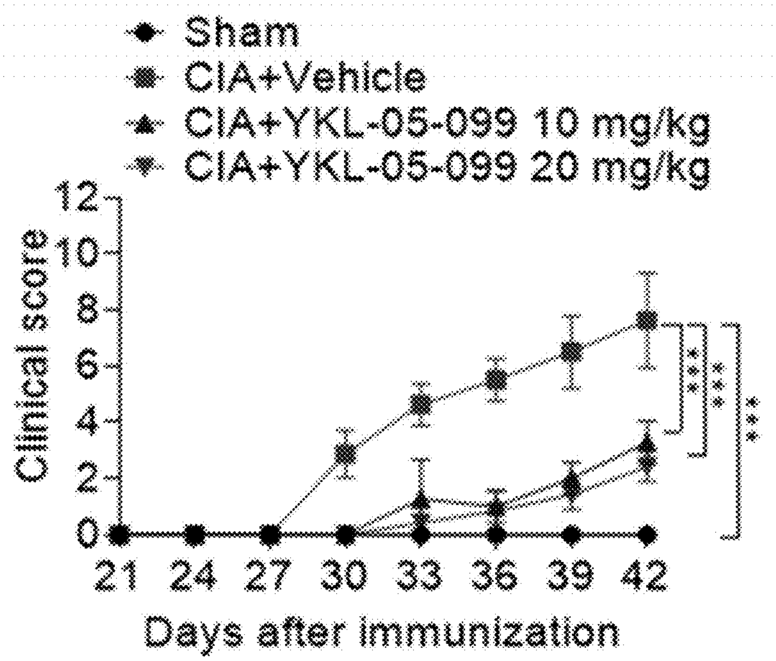
FIG. 6 illustrates clinical score in CIA mice in the embodiments of the present invention.
Figure 7:
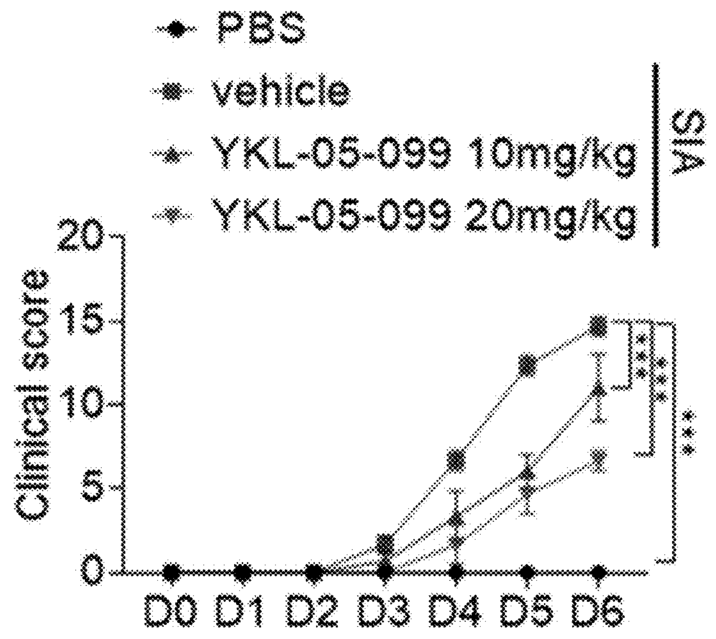
FIG. 7 illustrates clinical score in SIA mice in the embodiments of the present invention.

With regard to rheumatoid arthritis animal models CIA and SIA, respectively, rheumatoid arthritis clinical score was investigated. Disease-free mice without administration of antigen were used as a negative control. The clinical scores were determined depending on significance as follows: 0 (no symptom); 1 (slight edema on the soles or toes); 2 (significant edema throughout the soles and toes); 3 (significant to serious edema throughout the paw); 4 (serious edema and distortion throughout the paw), and then, the results for four paws were combined. FIG. 6 illustrates the results for CIA mice, and FIG. 7 illustrates the results for SIA mice, respectively. When YKL-05-099 was administered in an amount of 10 mg/kg or 20 mg/kg, it could be seen that the rheumatoid arthritis clinical scores were significantly reduced.

3. Mitigation Effects of Expansion of Spleen and Lymph Tissues

Figure 8:
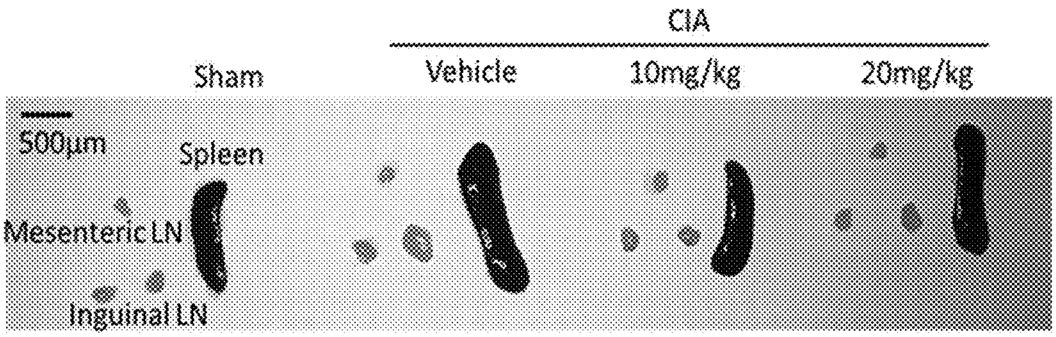
FIG. 8 is a photograph showing mitigation effects of expansion of the spleen and lymph nodes in the embodiments of the present invention.

As a result of comparing sizes of inguinal lymph node and mesenteric lymph node, which are the draining lymph nodes (DLNs) moving to the paw tissues, it could be confirmed that expansion of the spleen and the lymph nodes was greatly suppressed as compared to the control. Disease-free mice without administration of antigens were used as a negative control, and the compared results are shown in FIG. 8.

4. Bone Loss Inhibitory Effects Around Joint

Figure 9:
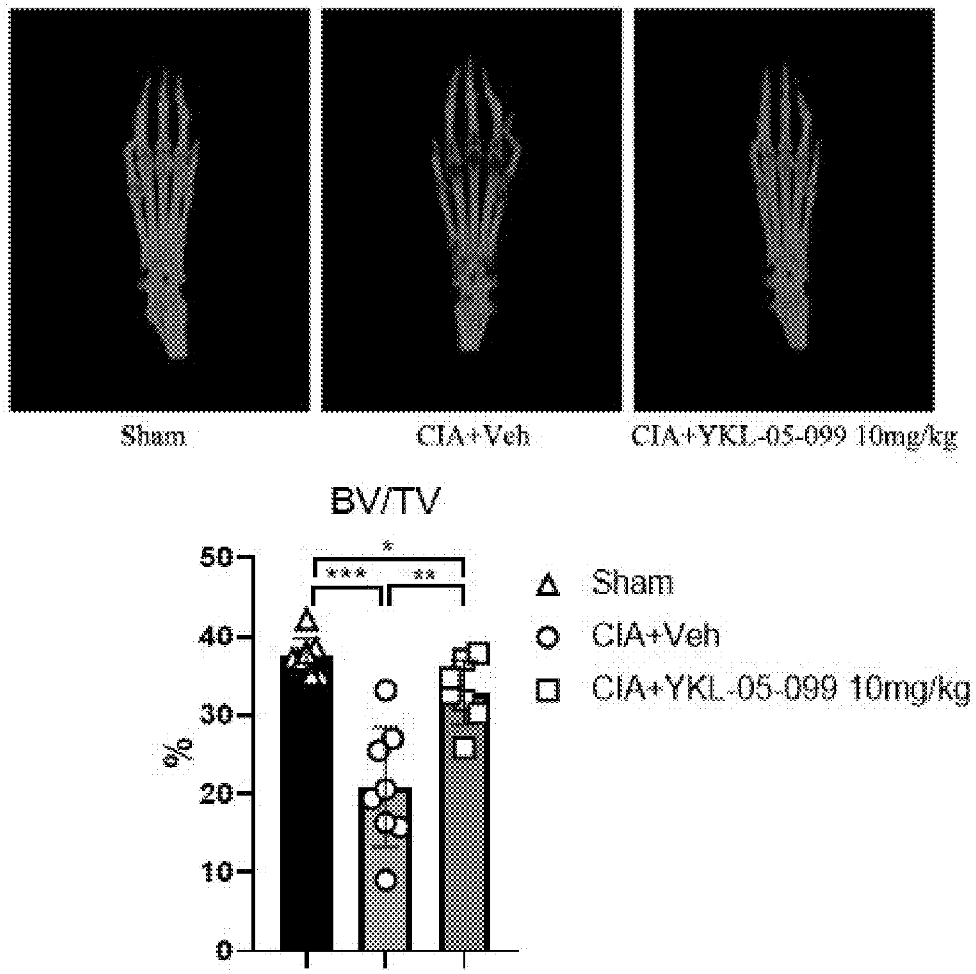
FIG. 9 is photographs taken through micro CT and graphs showing effects of inhibiting reduction of bone loss around the joints in the embodiments of the present invention.

In order to confirm whether YKL-05-099 administration may efficiently inhibit bone loss in a paw joint, which is one of representative symptoms of rheumatoid arthritis, a bone amount in the paw joint of a mouse was measured. As compared to the disease-free mice without administration of antigen as the negative control, rheumatoid arthritis mouse model CIA showed significant increase in bone loss. Further, it could be confirmed from FIG. 9 that bone loss was significantly inhibited in the YKL-05-099 administered mouse.

5. Mitigation Effects of Increase in Inflammatory Cytokine in the Blood

Figure 10:
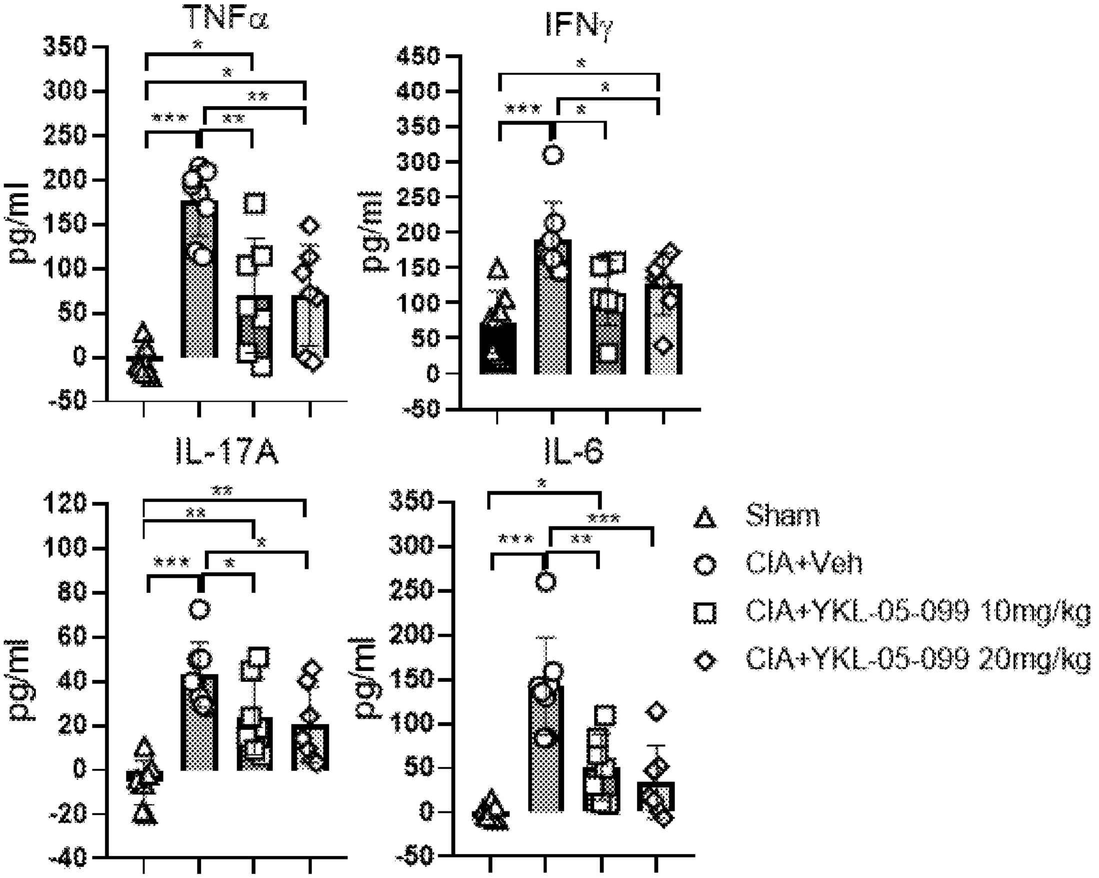
FIG. 10 illustrates measured results of cytokines of CIA mice in the embodiments of the present invention.
Figure 11:
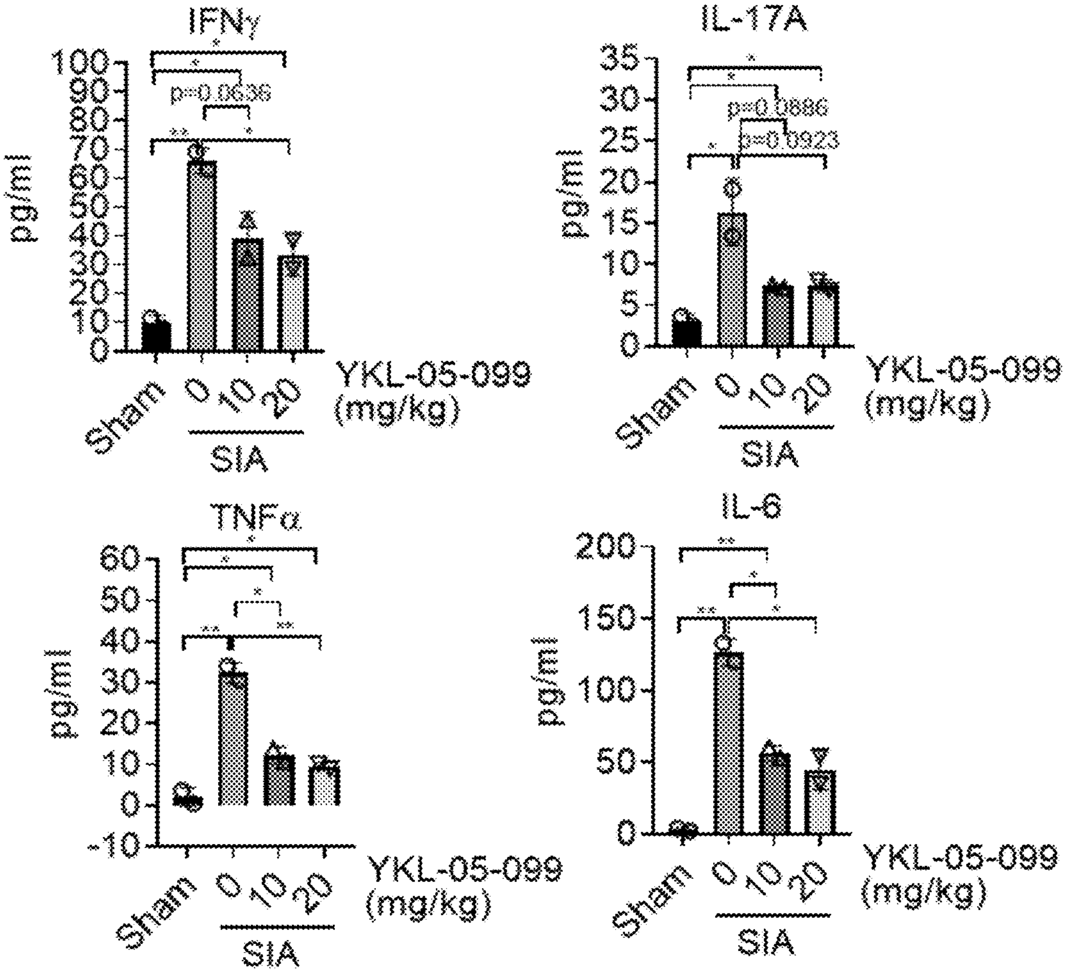
FIG. 11 illustrates measured results of cytokines of SIA mice in the embodiments of the present invention.

After administering YKL-05-099 to the rheumatoid arthritis animal model, essential inflammatory cytokines to induce rheumatoid arthritis such as TNF-α and IL-6, the representative immunoreactive cytokine of TH1 such as IFN-γ, and the representative immunoreactive cytokine of TH17 such as 1L-17a within peripheral blood at a time of sacrificing the mouse were subjected to analysis through enzyme linked immunosorbent assay (ELISA). Specifically, cytokine analysis was implemented using ELISA kit products according to instructions of Invitrogen Co., wherein the used product serial numbers are anti-IFN-γ (88-7314), anti-TNF-α (88-7324), anti-IL-17a (88-7371) and anti-IL-6 (88-7064). Disease-free mice without administration of antigens were used as a negative control. As compared to the negative control, the rheumatoid arthritis model mice showed increase in levels of major inflammatory cytokines of rheumatoid arthritis such as TNF-α, IL-6, TH1 and TH17, as well as levels of immunoreactive cytokines such as IFN-γ and IL-17a within the peripheral blood, in addition, it could also be confirmed that, when YKL-05-099 was administered, the inflammatory cytokines were greatly suppressed. FIG. 10 illustrates measured results of cytokines in CIA mice while FIG. 11 illustrates measured results of cytokines in SIA mice, respectively.

6. Mitigation Effects of Decrease in Regulatory T Cells

After i.p. administration of YKL-05-099 in an amount of 10 mg/kg or 20 mg/kg to the rheumatoid arthritis model CIA mice once a day, spleen cells were isolated at a time of sacrificing the mice to investigate Treg cell levels. Immune cell assay was performed through flow cytometry, and the experiment was implemented according to product instructions of Invitrogen Co. Specifically, the spleen cells were isolated to prepare $1\times10^6$ cells/100 μl of single cells, followed by staining live/dead cells using fixable viability dye (Invitrogen, eFluor™780, 65-0865-14), and then blocking the same using anti-CD16/32 (Invitrogen, 14-0161). Following this, the above product was stained using anti-CD4 (Invitrogen, RM4-5, mice) and anti-Foxp3 (Invitrogen, FJK-16s, mice). The stained cells were subjected to measurement of a ratio of $CD4^+$ $Foxp3^+$ cells as a marker for Treg in live cells isolated through flow cytometry.

Figure 12A:
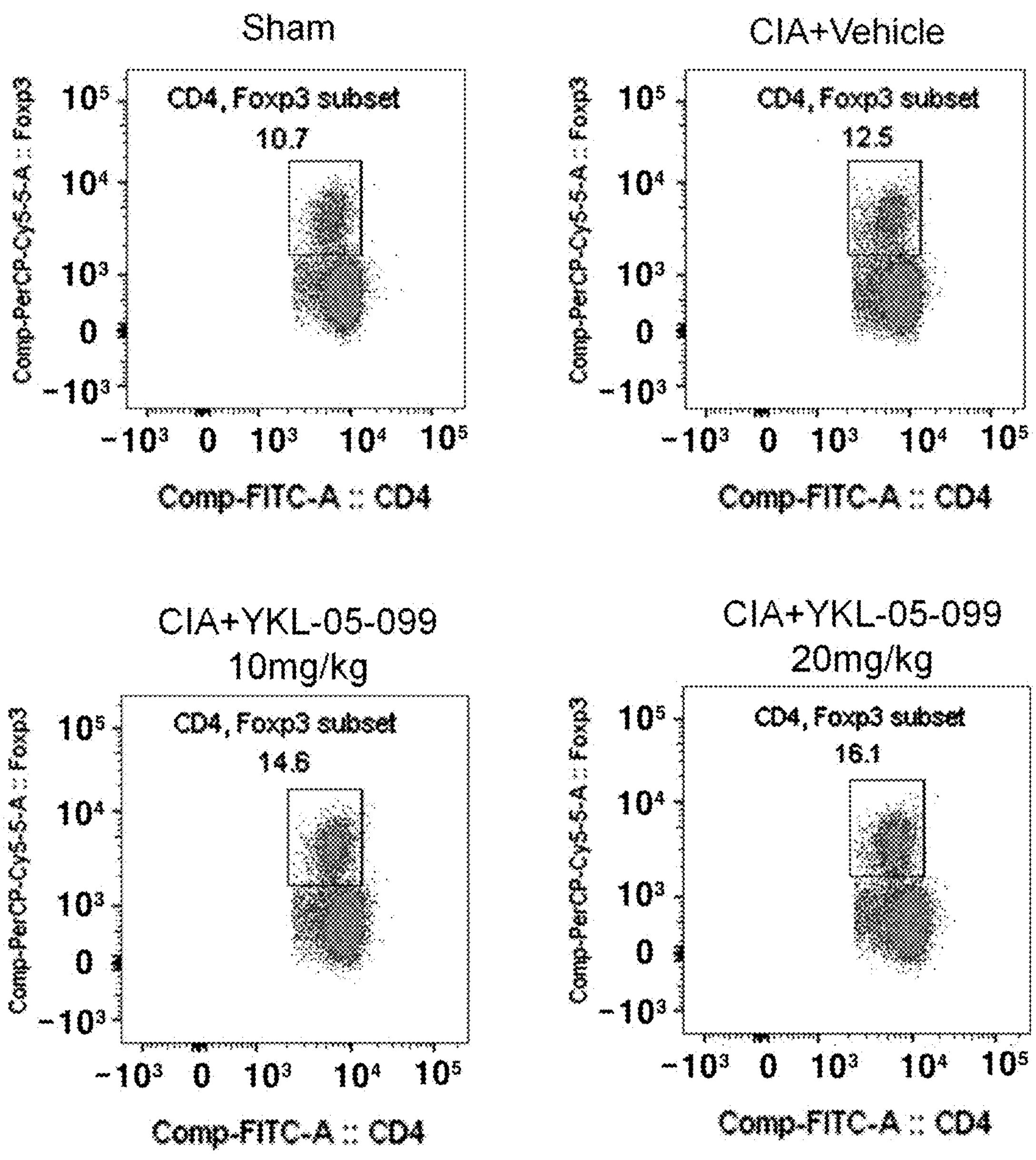
FIGS. 12A and 12B illustrate measured results of Treg cell level in the embodiments of the present invention.
Figure 12B:
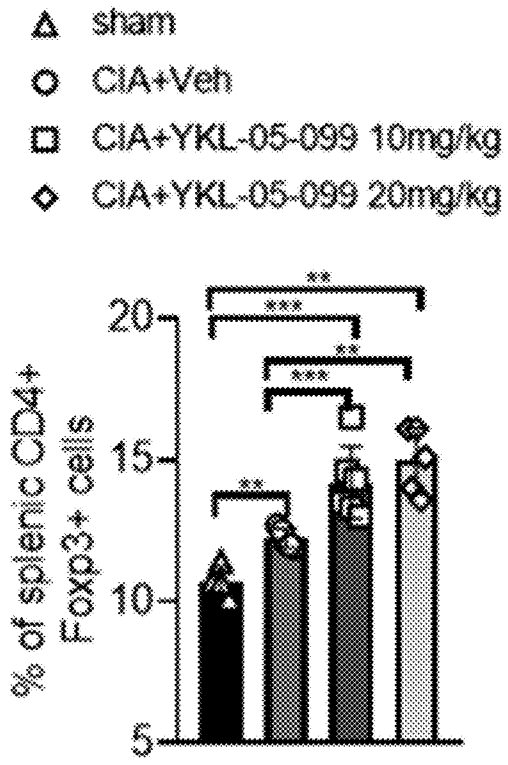

FIGS. 12A and 12B illustrate the above measured results. From the results of measuring a ratio of $CD4^+$ $Foxp3^+$ cells as a marker for Treg, it was confirmed that sham (disease-free mice) is 10.725±0.53%, CIA+Veh is 12.24±0.34%, CIA+YKL-05-099 10 mg/kg is 14.2±1.28%, CIA+YKL-05-099 20 mg/kg is 14.98±1.16%, respectively. Using unpaid parametric Welch's corrected t-test (two-tailed), p-value was indicated. With regard to statistically significant levels, p-value is 0.05 or less, wherein significance was represented by *$p<0.05$, $p<0.01$ and *$p<0.001$. Sham vs CIA+Veh p-value is 0.0045, CIA+YKL-05-099 10 mg/kg vs CIA+Veh p-value is 0.0119, CIA+YKL-05-099 20 mg/kg vs CIA+Veh p-value is 0.0046, CIA+YKL-05-099 10 mg/kg vs sham p-value is 0.0005, and CIA_YKL-05-099 20 mg/kg vs sham p-value is 0.0004. Consequently, it was confirmed that CIA+YKL-05-099 10 mg/kg and 20 mg/kg exhibit statistically significant increase in a ratio of Treg cells compared to CIA+Veh.

7. Mitigation Effects of Increase in Macrophage Cells

Figure 13A:
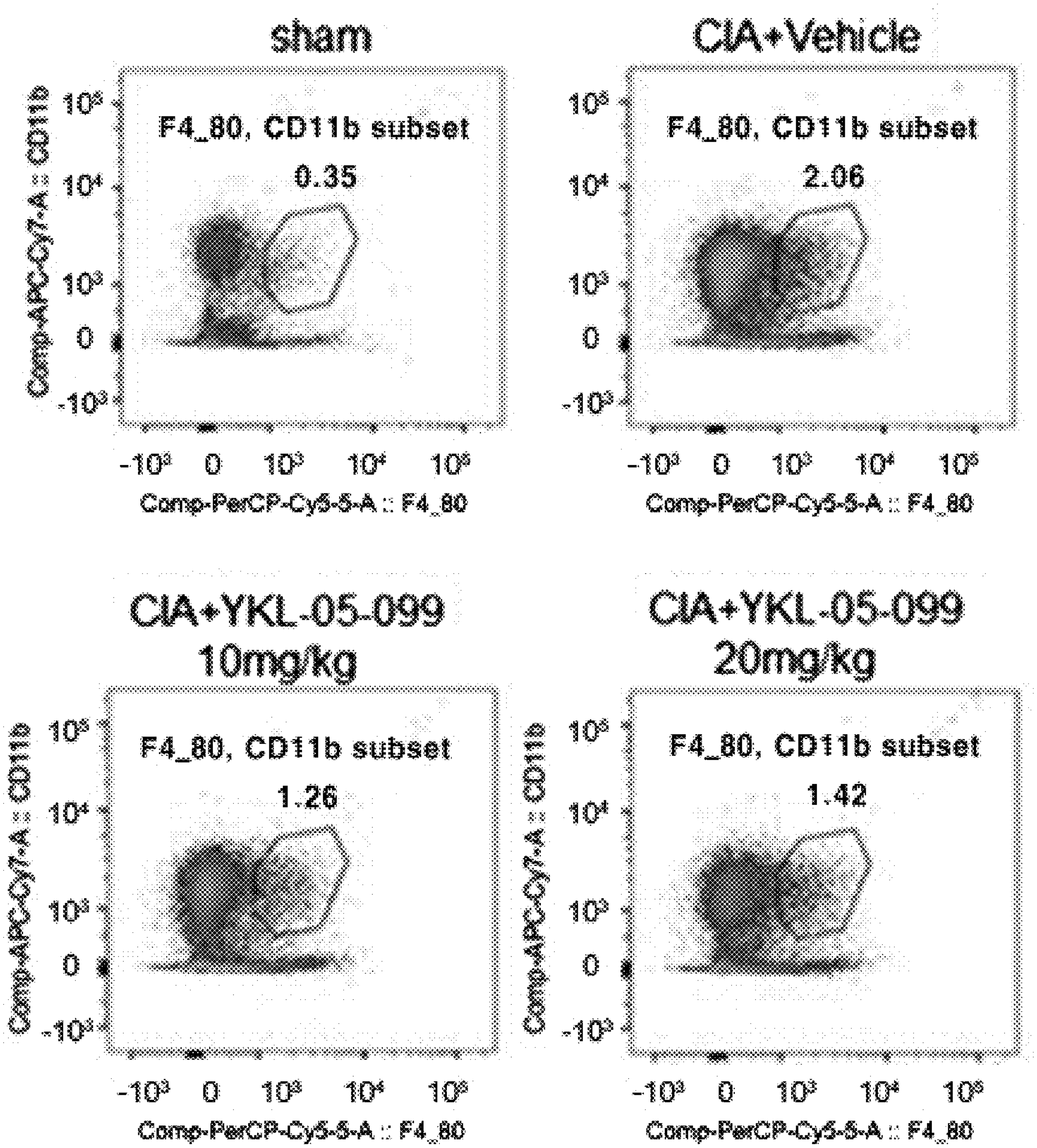
FIGS. 13A and 13B illustrate measured results of macrophage level in the embodiments of the present invent ion.
Figure 13B:
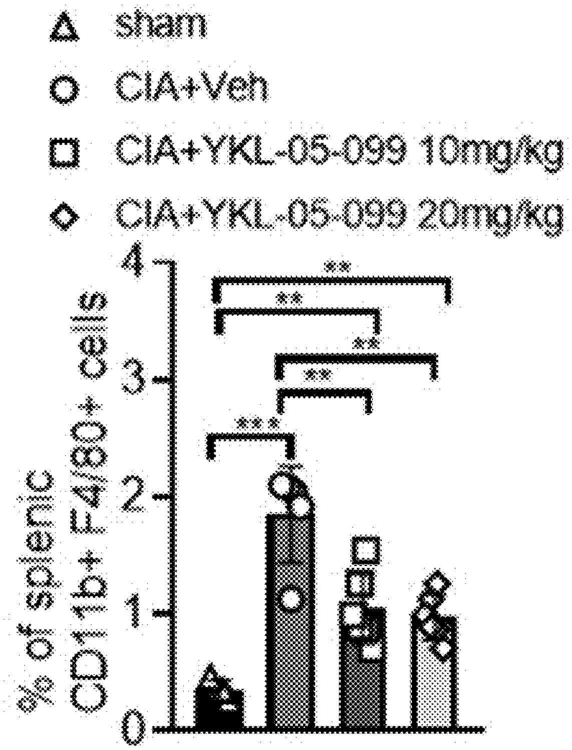

In order to confirm mitigation effects of increase in immune active macrophage cells in the spleen, after i.p. administration of YKL-05-099 in an amount of 10 mg/kg or 20 mg/kg to the rheumatoid arthritis model CIA mice once a day, spleen cells were isolated at a time of sacrificing the mice to investigate macrophage cell levels. FIGS. 13A and 13B illustrate the above results of investigating macrophage cell levels. Immune cell assay was performed through flow cytometry, and the experiment was implemented according to product instructions of Invitrogen Co.

Specifically, the spleen cells were isolated to prepare $1\times10^6$ cells/100 μl of single cells, followed by staining live/dead cells using fixable viability dye (Invitrogen, eFluor™780, 65-0865-14), and then blocking the same using anti-CD16/32 (Invitrogen, 14-0161). Following this, the above product was stained using anti-CD11b (Invitrogen, M1/70) and anti-F4/80 (Invitrogen, BM8). The stained cells were subjected to measurement of a ratio of $CD11b^+$ F4/80+ cells as a marker for macrophage cells in live cells isolated through flow cytometry.

From the result of measuring a ratio of CD11b+ F4/80+ cells as a marker for macrophage cells, it was confirmed that sham is 0.355±0.08%, CIA+Veh is 1.854±0.41%, CIA+YKL-05-099 10 mg/kg is 1.043±0.30%, CIA+YKL-05-099 20 mg/kg is 0.975±0.12%, respectively. Using unpaid parametric Welch's corrected t-test (two-tailed), p-value was indicated. With regard to statistically significant levels, p-value is 0.05 or less, wherein significance was represented by $^*p<0.05$, $^{}p<0.01$ and $^{*}p<0.001$. CIA+Veh vs sham p-value is 0.0009, CIA+YKL-05-099 20 mg/kg vs CIA+Veh p-value is 0.0057, CIA+YKL-05-099 10 mg/kg vs sham p-value is 0.0019, CIA+YKL-05-099 20 mg/kg vs sham p-value is 0.0002, and CIA+YKL-05-099 10 mg/kg vs CIA+Veh p-value is 0.0076. Further, it could be confirmed that CIA+YKL-05-099 10 mg/kg and 20 mg/kg exhibit statistically significant decrease in a ratio of macrophage cells compared to CIA+Veh.

What is claimed is:

1. A method for treatment of rheumatoid arthritis, the method comprising:

administering a pharmaceutical composition comprising a compound represented by Formula 1 below or a pharmaceutically acceptable salt thereof to a subject in need thereof:

[Formula 1]

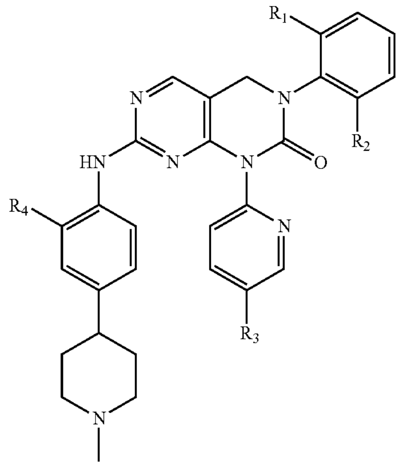

wherein $R_1$ and $R_2$ are each independently a halogen element or an alkyl group having 1 to 6 carbons; and $R_3$ and $R_4$ are each independently an alkoxy group having 1 to 6 carbons.

2. The method of claim 1, wherein the compound in the composition is administered in an amount of 0.8 to 1.6 mg per 1 kg by weight of the subject in need of administration once each day.

* * * * *